United States Patent [19]

Wiechert et al.

[11] 4,291,029
[45] Sep. 22, 1981

[54] 6β,7β;15,16-DIMETHYLENE-1,4-ANDROSTADIEN-3-ONES, THEIR PREPARATION AND USE AS MEDICINAL AGENTS

[75] Inventors: Rudolf Wiechert; Dieter Bittler; Ulrich Kerb; Klaus Prezewowsky; Jorge Casals-Stenzel; Wolfgang Losert, all of Berlin, Fed. Rep. of Germany

[73] Assignee: Schering, Aktiengesellschaft, Berlin and Bergkamen, Fed. Rep. of Germany

[21] Appl. No.: 154,194

[22] Filed: May 29, 1980

[30] Foreign Application Priority Data

May 31, 1979 [DE] Fed. Rep. of Germany ....... 2922500

[51] Int. Cl.³ .......................... A61K 31/33; C07J 1/00
[52] U.S. Cl. .............................. 424/238; 260/239.57; 260/397.1; 260/397.4; 424/243; 424/241
[58] Field of Search ............ 260/239.57, 397.4, 397.1; 424/238

[56] References Cited

U.S. PATENT DOCUMENTS 3,254,074  5/1966  Arth et al. ...................... 260/239.57
4,129,564 12/1978  Wiechert et al. ............... 260/239.57
4,180,570 12/1979  Wiechert et al. ................ 260/397.4

Primary Examiner—Elbert L. Roberts
Attorney, Agent, or Firm—Millen & White

[57] ABSTRACT

Compounds of the formula

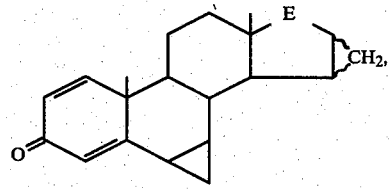

wherein
the 15,16-methylene group is in the α- or β-position, and
E is

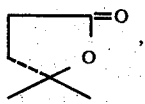

,

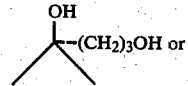

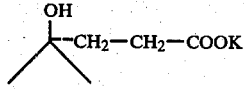

are useful as diuretics.

10 Claims, No Drawings

6β,7β;15,16-DIMETHYLENE-1,4-ANDROSTADIEN-3-ONES, THEIR PREPARATION AND USE AS MEDICINAL AGENTS

The present invention relates to novel adrostadienes having medicinal properties.

SUMMARY OF THE INVENTION

It is an object of this invention to provide new androstadienes having valuable pharmacological properties.

Upon further study of the specification and appended claims, further objects and advantages of this invention will become apparent to those skilled in the art.

These objects have been achieved by this invention in one aspect by providing 6β,7β;15,16-dimethylene-1,4-androstadien-3-ones of the formula

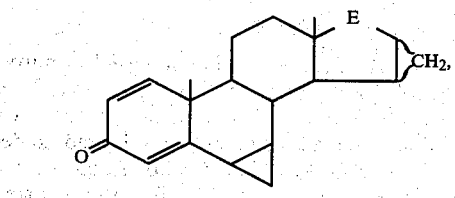

wherein
the 15,16-methylene group can be in the α- or β-position, and
E is

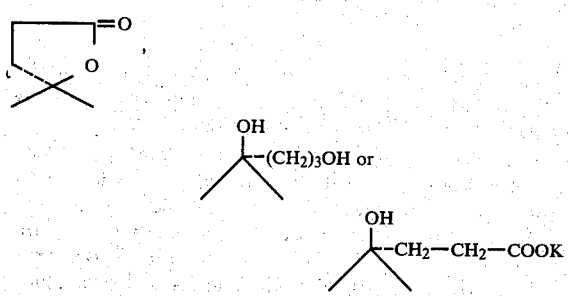

In another aspect, they have been achieved by providing methods for the medicinal use of these compounds.

DETAILED DISCUSSION

The present invention relates furthermore to a process for preparing 6β,7β;15,16-dimethylene-1,4-androstadien-3-ones of the formula

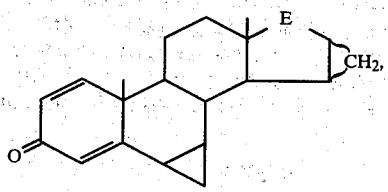

wherein
the 15,16-methylene group can be in the α- or β-position, and
E is

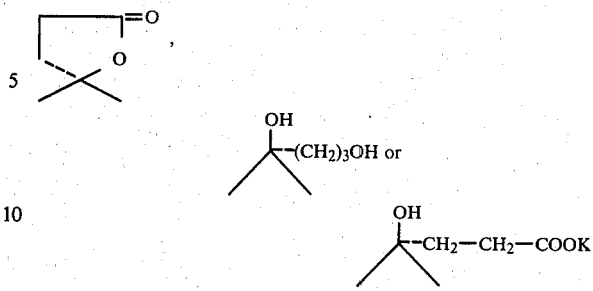

comprising introducing, in a conventional manner, a $\Delta^1$-double bond into the corresponding 6β,7β;15,16-dimethylene-4-androsten-3-ones, and, subsequently, optionally splitting a lactone ring when present.

The introduction of the $\Delta^1$-double bond is accomplished by conventional chemical or microbiological methods. Suitable chemical dehydrogenation agents for the 1,2-dehydrogenation include, for example, selenium dioxide, 2,3-dichloro-5,6-dicyanobenzoquinone, chloranil, thallium triacetate, lead tetraacetate, etc. Suitable microorganisms for the 1,2-dehydrogenation include, for example, schizomycetes, especially those of the genera Arthrobacter, e.g., *A. simplex* ATCC 6946; Bacillus, e.g., *B. lentus* ATCC 13805 and *B. sphaericus* ATCC 7055; Pseudomonas, e.g., *P. aeruginosa* IFO 3505; Flavobacterium, e.g., *F. flavescens* IFO 3058; Lactobacillus, e.g., *L. Brevis* IFO 3345; and Nocardia, e.g., *N. opaca* ATCC 4276. The microbiological process is conducted using fully conventional conditions and methods, e.g., as disclosed in A. Capec et al, Microbial Transformation of Steroids, Academic Press, Prague 1966, especially pages 65-68, whose disclosure is incorporated by reference herein.

The 1,2-dehydrogenation is preferably executed by a chemical process. For this purpose, the 1,2-dihydro steroid is heated for a relatively long period of time in a suitable solvent with the dehydrogenating agent. Suitable solvents include, for example, dioxane, tert-butanol, tetrahydrofuran, toluene, benzene, etc. or mixtures thereof.

The reaction is generally conducted at 70°-120° C. and is terminated after several hours, e.g., 3-20 hours. It is advantageous to observe the reaction by thin-layer chromatography. The reaction mixture is worked up once the starting material has been converted.

The optionally following opening of the lactone ring likewise takes place according to conventional methods. For example, for this purpose, the lactone can be heated (e.g., to 20°-50° C. for ¼-3 hours) with dilute potassium hydroxide solution, thus producing the potassium salt of the 3-substituted propionic acid.

After the reaction is completed, the reaction mixture is worked up as usual, such as by precipitation, extraction, recrystallization and/or chromatography, etc.

The preparation of the 1,2-hydrogenated steroid starting materials is described in U.S. Pat. No. 4,129,564 (Wiechert et al.).

The compounds of this invention possess valuable pharmacological properties. They are, inter alia, diuretics of the type of the aldosterone antagonists, i.e., they reverse the effect of deoxycorticosterone on the elimination of sodium and potassium. The compounds of this invention surprisingly prove to be superior to the conventional spironolactone in the test model by Hollmann (G. Hollmann et al, "Tubuläre Wirkungen und renale Elimination von Spirolactonen" [Tubular Effects and Renal Elimination of Spirolactones], Naunyn-Schmiedebergs Arch. Exp. Path. Pharmak. 247:419 [1964]; P. Marx, "Renale Wirkungen des d-Aldosterons und seines Antagonisten Spironolactons" [Renal Effects of d-Aldosterone and Its Antagonist Spirolactone], Diss. Med. Fak. FU Berlin [Medical Dissertation of the Faculty, Berlin Free University] 1966).

The compounds of this invention are utilized in accordance with conventional methods of galenic pharmacy for the preparation of medicinal agents for oral and parenteral administration.

The pharmacologically active compounds of this invention can be processed in accordance with conventional methods of galenic pharmacy to produce medicinal agents, for, e.g., oral and parenteral administration to patients, e.g., mammals including humans. Conventional excipients are pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, polyethylene glycols, gelatine, lactose, amylose, magnesium stearate, talc, silicic acid, fatty acid monoglycerids and diglycerides, pentaerythritol fatty acid esters, hydroxymethylcellulose, polyvinyl pyrrolidone, etc. The pharmaceutical preparation can be sterilized and if desired mixed with auxiliary agents, e.g., lubricants, preservatives, stabilizers, wetting agents, emulsifiers, salts for influencing osmotic pressure, buffers and/or coloring, substances and the like which do not deleteriously react with the active compounds.

For parenteral application, particularly suitable are injectable sterile solutions, preferably aqueous solutions.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed.

Generally, the compounds of this invention are dispensed in unit dosage form comprising 10–100 mg. in a pharmaceutically acceptable carrier per unit dosage.

The dosage of the compounds according to this invention is 10–200 mg./day when administered to patients, e.g., humans, e.g., as a diuretic, in the same manner as the known aldosterone antagonist, spironolactone. In terms of body weight, suitable dosages are 0.1–3 mg/kg/day.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

500 mg of 6β,7β;15β,16β-dimethylene-4-androstene-[17(β-1′)-spiro-5′]perhydrofuran-2′,3-dione is heated under reflux for 17 hours in 7.5 ml of dioxane with 500 mg of 2,3-dichloro-5,6-dicyano-p-benzoquinone. The mixture is then diluted with ether, washed with saturated sodium bicarbonate solution and water, dried, and evaporated. The residue is chromatographed on silica gel, thus obtaining 330 mg of 6β,7β;15β,16β-dimethylene-1,4-androstadiene[17(β-1′)-spiro-5′]perhydrofuran-2′,3-dione, m.p. 250.5°–252° C.

UV: $\epsilon_{245} = 12,000$, $\epsilon_{286} = 9,950$.

EXAMPLE 2

300 mg of 6β,7β;15α,16α-dimethylene-4-androstene-[17(β-1′)-spiro-5′]perhydrofuran-2′,3-dione is stirred under reflux in 15 ml of tert.-butanol for 20 hours with 90 mg of selenium dioxide and 0.5 ml of acetic acid. Another 90 mg of selenium dioxide is then added, and the mixture is heated under reflux for another 24 hours. After evaporation to dryness, the residue is chromatographed on silica gel, thus producing 120 mg of 6β,7β;15α,16α-dimethylene-1,4-androstadiene-[17(β-1′)-spiro-5′]perhydrofuran-2′,3-dione.

UV: $\epsilon_{245} = 11,800$, $\epsilon_{285} = 9,800$.

EXAMPLE 3

500 mg of 6β,7β;15β,16β-dimethylene-1,4-androstadiene[17(β-1′)-spiro-5′]perhydrofuran-2′,3-dione is combined in 5 ml of isopropanol with 1.37 ml of 1N potassium hydroxide in methanol and heated under reflux for 1 hour. After cooling, 30 ml of absolute ether is added to the reaction mixture, and the latter is stirred for another hour in an ice bath. The thus-crystallized precipitate is vacuum-filtered, thoroughly washed with ether, and dried, thus obtaining 510 mg of 3-(17β-hydroxy-6β,7β;15β,16β-dimethylene-3-oxo-1,4-androstadien-17α-yl)propionic acid potassium salt.

UV: $\epsilon_{245} = 11,500$; $_{286} = 9,600$.

EXAMPLE 4

300 mg of 17β-hydroxy-17α-(3-hydroxypropyl)-6β,7β;15β,16β-dimethylene-4-androsten-3-one is heated under reflux in 9 ml of dioxane for 17 hours with 300 mg of 2,3-dichloro-5,6-dicyano-p-benzoquinone. The mixture is then diluted with ether, washed with saturated sodium bicarbonate solution and water, dried, and evaporated. The residue is chromatographed on silica gel. 120 mg of 17β-hydroxy-17α-(3-hydroxypropyl)-6β,7β;15β,16β-dimethylene-1,4-androstadien-3-one is obtained as an amorphous compound.

UV: $\epsilon_{244} = 11,500$; $\epsilon_{285} = 9,600$.

EXAMPLE 5

10.0 mg. of 6β,7β;15,16β-dimethylene-1,4-androstadiene[17(β-1′)-spiro-5′]perhydrofuran-2′,3-dione are micronised (finely ground) and homogeneously mixed with:
- 80.0 mg. lactose (DAB (German Pharmacopoeia 7); USP XVII),
- 29,6 mg. microcristallin cellulose, and
- 0,4 mg. magnesium stearate (USP XVII), and compressed into tablets without previous granulation, these tablets having a weight of 120 mg., with a diameter of about 7 mm. and a thickness of 2.7–2.9 mm.

EXAMPLE 6

25.0 mg. of 6β,7β;15,16β-dimethylene-1,4-androstadiene[17(β-1′)-spiro-5′]perhydrofuran-2′,3-dione is compressed, analogously to Example 5, into tablets having a final weight of 150 mg. with:
- 80.0 mg. lactose (DAB 7), 6.0 mg. poly-N-vinylpyrrolidone 25,
36.4 mg. corn starch (DAB 7),
2.0 mg. talc, and
0.6 mg. magnesium stearate (USP XVII).

EXAMPLE 7

50.0 mg of 17β-hydroxy-17alpha-(3-hydroxypropyl)-6β,7β;15β; 16β-dimethylene-1,4-androstadien-3-one (micronized, particle size 2-8 μm) are mixed homogeneously with 150 mg. of lactose (USP XVII) and filled into hard-gelatin capsules (6×16 mm).

EXAMPLE 8

Respectively 100.0 mg. of 6β,7β; 15alpha,16alphadimethylene-1,4-androstadiene/17(β-1')-spiro-5'/perhydrofuran-2',3-dione are mixed homogeneously with 400.0 mg of lactose (USP XVII) and filled into hard-gelatin capsules (8×22 mm).

EXAMPLE 9

In order to prepare an injection solution, 50.0 mg. of 3-(17β-hydroxy-6β,7β;15β,16β-dimethylene-3-oxo-1,4-androstadien-17alpha-yl)propionic acid potassium salt are dissolved in water for injection, filtered under aseptic conditions into a brown coloured injection bottle, freeze-dried and sealed by a rubber stopper and a borderded capsule.

Before administration, the stopper is pierced by the cannula of a syringe containing 10 ml. of water for injection, the water is injected into the bottle, the substance is dissolved by slight shaking the bottle, and the injection solution is re-sucked into the syringe.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 6β,7β;15,16-dimethylene-1,4-androstadien-3-one of the formula

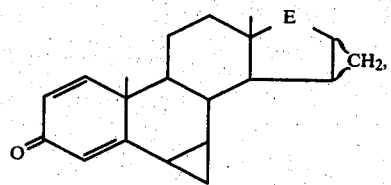

wherein the 15,16-methylene group is in the α- or β-position, and

E is

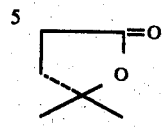

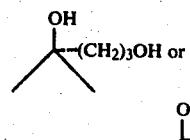

or

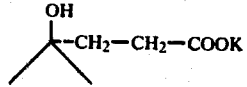

2. 6β,7β;15β,16β-Dimethylene-1,4-androstadiene-[17(β-1')-spiro-5']perhydrofuran-2',3-dione, a compound of claim 1.

3. 6β,7β;15α,16α-Dimethylene-1,4-androstadiene-[17(β-1')-spiro-5']perhydrofuran-2',3-dione, a compound of claim 1.

4. 3-(17β-Hydroxy-6β,7β;15β,16β-dimethylene-3-oxo-1,4-androstadien-17α-yl)propionic acid potassium salt, a compound of claim 1.

5. 17β-Hydroxy-17α-(3-hydroxypropyl)-6β,7β;15β,16β-dimethylene-1,4-androstadien-3-one, a compound of claim 1.

6. A pharmaceutical composition comprising a diuretically effective amount of a compound of claim 1 and a pharmaceutically acceptable carrier.

7. A method of achieving a diuretic effect in a patient in need of such treatment comprising administering to the patient a diuretically effective amount of a compound of claim 1.

8. A compound of claim 1 wherein E is

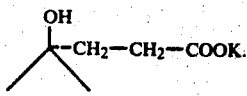

9. A compound of claim 1 wherein E is

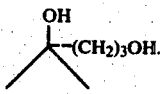

10. A compound of claim 1 wherein E is

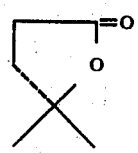

* * * * *